United States Patent [19]

Shearer et al.

[11] Patent Number: 5,462,563
[45] Date of Patent: Oct. 31, 1995

[54] ORTHOPAEDIC IMPLANT

[75] Inventors: John R. Shearer, Southampton; Philip Shelley, Sheffield, both of England

[73] Assignee: Minnesota Mining and Manufacturing Company, St. Paul, Minn.

[21] Appl. No.: 308,945

[22] Filed: Sep. 20, 1994

Related U.S. Application Data

[63] Continuation of Ser. No. 35,906, Mar. 23, 1993, abandoned, which is a continuation of Ser. No. 822,619, Jan. 17, 1992, abandoned.

[30] Foreign Application Priority Data

Jan. 17, 1991 [GB] United Kingdom .................. 9101008

[51] Int. Cl.⁶ .................................................. A61F 2/40
[52] U.S. Cl. ........................................... 623/18; 623/19
[58] Field of Search ............................ 623/19, 18, 21, 623/23, 22, 16

[56] References Cited

U.S. PATENT DOCUMENTS

| | | | |
|---|---|---|---|
| 3,916,451 | 11/1975 | Buechel et al. | 3/1.91 |
| 3,978,528 | 9/1976 | Crep | 3/1.91 |
| 4,003,095 | 6/1977 | Gristina | 3/1.91 |
| 4,040,131 | 8/1977 | Gristina | 3/1.91 |
| 4,179,758 | 12/1979 | Gristina | 3/1.91 |
| 4,206,517 | 6/1980 | Pappas et al. | 3/1.91 |
| 4,219,893 | 9/1980 | Noiles | 3/1.91 |
| 4,279,041 | 7/1981 | Buchholz | 3/1.912 |
| 4,301,553 | 11/1981 | Noiles | 3/1.91 |
| 4,352,212 | 10/1982 | Greene et al. | 3/1.91 |
| 4,538,305 | 9/1985 | Engelbrecht et al. | 623/20 |
| 4,634,444 | 1/1987 | Noiles | 623/20 |
| 4,650,489 | 3/1987 | Thompson | 623/16 |
| 4,693,723 | 9/1987 | Gabard | 623/19 |
| 4,892,546 | 1/1990 | Kotz et al. | 623/18 |
| 4,908,032 | 3/1990 | Keller | 623/18 |
| 4,911,719 | 3/1990 | Merle | 623/18 |
| 4,919,669 | 4/1990 | Lannelongue | 623/19 |
| 4,986,833 | 1/1991 | Worland | 623/19 |

FOREIGN PATENT DOCUMENTS

| | | | |
|---|---|---|---|
| 0127503 | 4/1984 | European Pat. Off. | A61F 1/03 |
| 0278807 | 1/1988 | European Pat. Off. | A61F 2/40 |
| 0299889 | 7/1988 | European Pat. Off. | A61F 2/40 |
| 2647670 | 6/1989 | France | A61F 2/40 |
| 2932744 | 2/1990 | Germany | 623/22 |
| 1438950 | 6/1976 | United Kingdom | A61F 1/24 |
| 1548750 | 7/1979 | United Kingdom | A61F 1/24 |
| 2223172 | 4/1990 | United Kingdom | A61F 2/40 |

OTHER PUBLICATIONS

Declaration of John R. Shearer.
Glenohumeral Arthroplasty, pp. 148–150.

Primary Examiner—David Isabella
Assistant Examiner—Debra S. Brittingham
Attorney, Agent, or Firm—Gary L. Griswold; Walter N. Kirn; Stephen W. Bauer

[57] ABSTRACT

A humeral implant of the type that locates the head of a glenoid prosthesis relative to a patient's humerus, the implant comprising:

a socket cup adapted to receive the head of the glenoid prosthesis;

an elongate stem connected to the socket cup and a sleeve adapted to receive the elongate stem and allow axial and rotational movement of the elongate stem within the sleeve, the sleeve being adapted to be inserted and secured within the humerus of the patient.

16 Claims, 5 Drawing Sheets

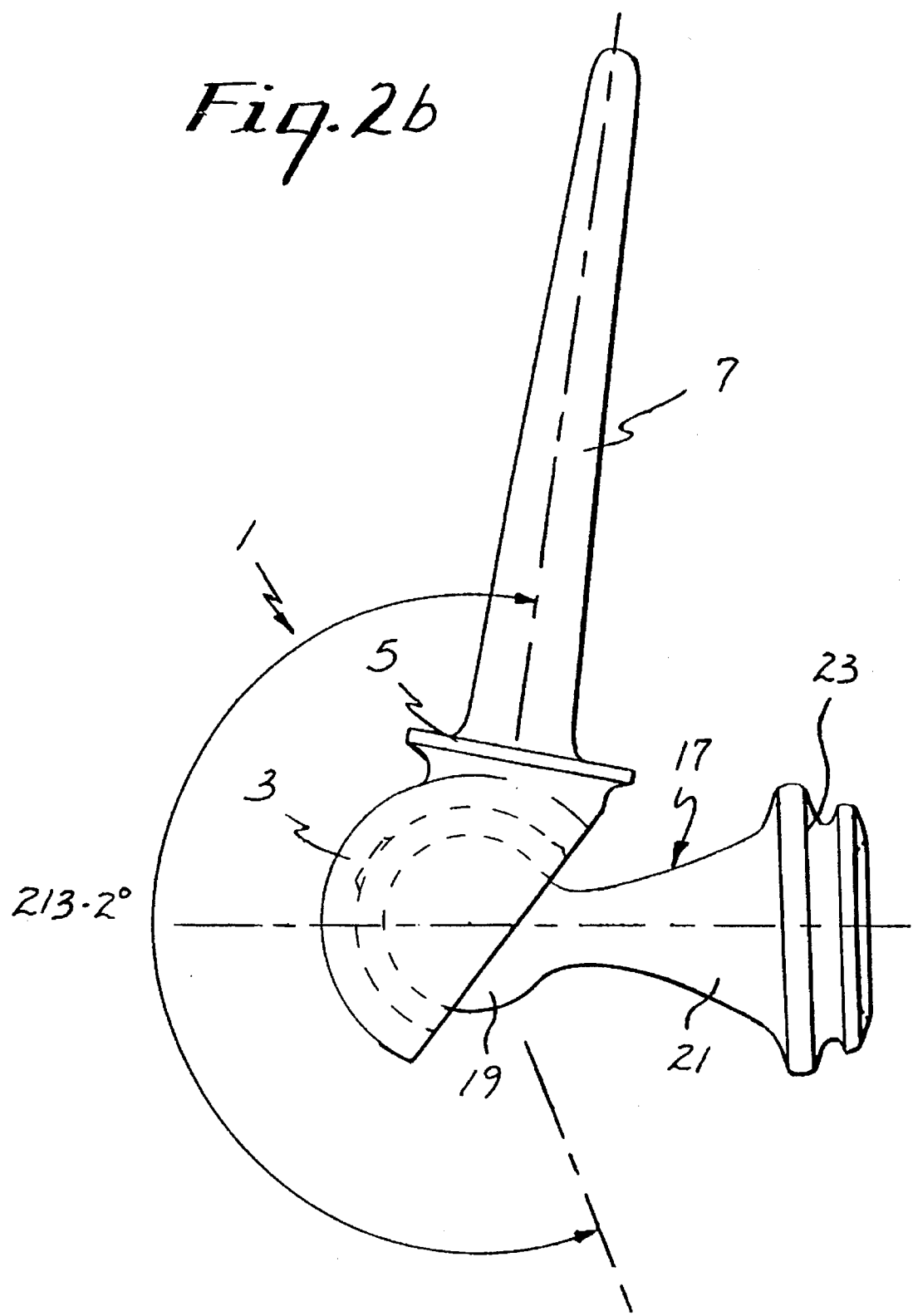

ORTHOPAEDIC IMPLANT

This is a continuation of application Ser. No. 08/035,906 filed Mar. 23, 1993, now abandoned, which is a continuation of application Ser. No. 07/822,619 filed Jan. 17, 1992, now abandoned.

FIELD OF THE INVENTION

This invention relates to orthopaedic implants and in particular to constrained shoulder joint replacements having improved triaxial articulation and increased resistance to dislocation.

BACKGROUND TO THE INVENTION

It is known that permanent reconstruction of a bone joint which has been malformed from birth, or as a result of disease, or accidental injury, may be achieved by the substitution of the afflicted portion(s) of the joint by an artificial implant constructed of a biocompatible material. It is desirable that any replacement joint should imitate the natural articulation of the healthy joint.

One method of replacing the shoulder joint has utilised a stemmed humeral prosthesis adapted to be inserted and retained within the medullary canal of the humerus after removal of the natural humeral head. The socket function of the replacement joint is performed by a glenoid cup implant which defines a spherical recess adapted to receive the ball end of the humeral prosthesis. Dislocation of the humeral ball is prevented by the soft tissue structures and the natural stability of the spherical recess. Examples of such implants are disclosed in EP-0216489 and U.S. Pat. No. 4,179,758. However, the dimensions of the glenoid cup are such that there is often insufficient bone tissue to permit the secure fixation of, or the reaming out of, a socket deep enough to contain a more constrained humeral ball.

This problem has led to the design of an 'inverted' ball-and-socket arrangement in which the socket is located in the proximal region of the humerus, whilst the corresponding ball articulation protrudes from the glenoid process. This reduces the amount of bone which needs to be removed from the glenoid in order to achieve a more constrained joint. The humeral component consists of a tapering shaft which fits into a reamed cavity within the humerus and on which is located the corresponding socket. A wider range of movements can be achieved using such an arrangement, with additional flexibility being imparted by the mobile anatomy of the scapula of which the glenoid is a part. Examples of such implants are disclosed in EP-0177503, EP-0299889, U.S. Pat. No. 3,916,451, U.S. Pat. No. 3,978,528 and GB 1438950. However, such implants still exhibit a significant reduction in the comfortable range of movements when compared to a normal shoulder joint, resulting in the transmission of considerable loosening forces to the implant/bone interfaces.

Any constrained joint of this type must have a 'captured' ball attached to the glenoid via a neck whose minimum thickness is governed by the mechanical strength of the material from which it is manufactured. This neck will interfere with the humerally located rim of the socket and this results in a reduction in the range of movements of the humerus, most notably in full abduction and/or rotation of the humerus. The thinner the neck, the less would be the interference and the greater the available range of movements. Known implants reduce this interference by angling the socket in the humerus, although this is found to compromise the medial movement in order to gain such additional extension. The socket must also surround more than a hemisphere of the ball in order to be constrained, thereby limiting articulation still further.

Furthermore, most known constrained shoulder implants require both the humeral and glenoidal components to be fixed rigidly into their corresponding bones, either by a tight press-fit, cemented or screw attachment. Without the ability to rotate the humerus completely around its longitudinal axis, due to muscle configuration and surrounding tissue, the arm cannot feasibly, or comfortably, be laterally raised from the horizontal to the vertical in a plane parallel to the frontal plane. The arm may be raised to the vertical in the sagittal plane only, and even then this might be expected to result in some abduction of the whole arm, i.e., lateral movement. Such large range of movements mean that impingement of known types of constrained shoulder implants is easily possible. Articular 'no-go' areas are potential regions of aggressive dislocation, by leverage, or implant damage if the humerus were forced violently into such an orientation.

U.S. Pat. No. 4,919,669 discloses a shoulder prosthesis of the type comprising a humeral piece intended to be fixed in a humerus to replace at least the head thereof. The humeral piece comprises a hollow tubular element which must be fixed in the humerus substantially along the longitudinal axis thereof and a cylindrical rod, the upper end of which carries a ball cooperating with a glenoid bearing surface to form the shoulder joint and the lower end of which is disposed in said tubular element. The rod is able to slide relative to the hollow tubular element. The glenoid bearing surface consists of a glenoid piece which comprises an anchoring element intended to be inserted into a cavity formed in the scapula and a female hemispherical element. The female hemispherical element cooperates with the male ball of the humeral piece.

British Patent No. 2,223,172 discloses a joint structure for use as a shoulder prosthesis comprising a first member which is implanted in an end of the humerus, a spherical member which is implanted in a socket in the scapula, and an intermediate member which can pivot relative to the first and second members about respective axes. These axes are mutually inclined (preferably at an angle in the region of 45°) and preferably intersect at a position in the intermediate member.

BRIEF SUMMARY OF THE INVENTION

A humeral prosthesis has now been designed for use in shoulder replacements having improved articulation and a reduced propensity for dislocation.

Therefore according to the present invention there is provided a humeral implant of the type that locates the head of a glenoid prosthesis relative to a patient's humerus, the implant comprising:

a socket cup adapted to receive the head of the glenoid prosthesis;

an elongate stem connected to the socket cup and a sleeve adapted to receive the elongate stem and allow movement of the elongate stem within the sleeve, the sleeve being adapted to be inserted and secured within the humerus of the patient.

The elongate stem of the humeral component is preferably capable of rotary movement within the outer sleeve and more preferably is capable of both rotary and axial movement within the outer sleeve.

The humeral implants of the invention are intended to form one component of a two unit inverted ball and socket joint. The socket cup of the humeral implant receives the ball end of a conventional glenoid prosthesis to constitute the complete joint.

The combination of an inverted ball and socket joint and the ability of the stem of the humeral implant to move relative to the humerus provides particular advantages compared with known implants.

The ability of the stem of the humeral component to rotate within the sleeve thereby rotating the socket cup, provides additional articulation compared with a static humeral implant and is found to improve the permissible range of movement of the humerus, while reducing the reliance on scapular compensation to a minimum. In a conventional anatomy shoulder joint the ball rotating in the humerus would not alter its geometry and the fixed glenoid cup would offer a fixed constraint to, say, abduction, as it is not able to rotate.

Shoulder joints incorporating implants of the invention are capable of reproducing the natural triaxial articulation of the normal shoulder joint. The combination of a non-integral stem and sleeve not only ensures a greater range of continuous movement but also serves as a measure of protection against violent dislocation by removing the inherent rigidity of known gleno-humeral shoulder replacements. Preferably the stem is permitted axial movement within the outer sleeve to absorb humeral distraction, thereby protecting the joint from potential dislocating forces, e.g., as may be experienced when carrying a heavy weight in the hand or the crook of the elbow, or in a fall.

The socket cup and stem are preferably formed of titanium or a titanium alloy, although other suitable biocompatible materials may also be used, such as wrought or cast cobalt-chromium alloys, e.g., vitallium, or stainless steel. Normally, the socket cup and stem are integrally formed. The implant may include a collar interposed between the socket cup and stem, the collar being dimensioned such that it abuts the end of the sleeve to prevent the stem forcing itself into the sleeve resulting in a loss of rotation.

The socket cup generally comprises a hemispherical shell defining a recess into which is fitted an inner liner of a plastics material, thereby providing a spherical bearing surface for receiving the ball portion of the glenoid component. The socket cup may be inclined at an angle to the longitudinal axis of the stem to minimise interference between the upper lip of the socket cup and the neck of the glenoid component. Although any angle between the diametrical plane of the socket cup and the longitudinal axis of the stem up to a maximum of about 45° may be used, the socket cup is preferably inclined at an angle from 20° to 40°.

The stem is fitted within the outer sleeve such that it is capable of unhindered rotation and is preferably capable of axial displacement. The stem is normally formed as a cylindrical or tapered elongate member with the sleeve having a complementary bore. A tapered stem generally has a taper of up to 15°, typically about 5°. Both the stem and bore of the sleeve must be accurately formed to prevent any unwanted lateral movement of the prosthesis. The stem must also be of a sufficient length to prevent its escape from the shaft of the sleeve under conditions of normal humeral distraction.

The sleeve of the implant is adapted to be inserted into the reamed medullary cavity of the patient's humerus, which will determine the external shape and configuration of the sleeve. While, the sleeve may be cemented or screwed into position, it is preferred to fabricate the sleeve of a biocompatible material formed with an attachment surface capable of receiving an ingrowth of bone tissue which will serve to anchor the implant in position. This arrangement dispenses with the need for cements which have been found to have a deleterious action on bone tissue. However, some biocompatible materials able to promote tissue ingrowth are not always the most suitable materials for allowing efficient rotation of the stem within the sleeve. Thus, although an implant may incorporate a single sleeve, it is preferred to use a combination of inner and outer sleeves thereby avoiding the problem of fabricating a single sleeve having inner and outer surfaces possessing different properties. By using two sleeves, it is possible to fabricate the outer sleeve of a suitable biocompatible material, such as titanium, and the inner sleeve of a material capable of reducing friction and wear during rotation of the stem. A preferred combination comprises a titanium or a titanium alloy stem and an inner sleeve formed of a high density plastics material, such as polyethylene. The stem may also be treated to reduce friction, e.g., by fine polishing and/or coating with a 'non-stick' anti-friction material. While it is essential that the stem should be free to move, preferably rotate, within the inner sleeve, it is desirable that the inner sleeve should not be capable of independent movement for efficient joint function. This may be achieved by roughening, e.g., by blasting, the inner surface of the outer sleeve (and optionally the outer surface of the inner sleeve), thereby increasing the adhesion of the sleeves to each other. Alternatively, the inner and outer sleeves may be provided with one or more interengaging ribs and stops.

In an alternative embodiment, an inner plastic sleeve may be securely fitted to the stem of the implant (by roughening the complementary surfaces thereof), the composite of stem and inner sleeve being rotatable within the outer sleeve.

It is preferred to treat those regions of the outer sleeve contacting the humeral bone tissue, to provide an attachment surface capable of receiving an ingrowth of bone tissue. The interaction of bone and sleeve provides for the cementless bonding of the sleeve into the reamed cavity of the humerus. Techniques are known in the art for the provision of such attachment surfaces, either by modification of an existing implant surface or by deposition of an external surface layer. However, it is preferred to use electro-discharge machining (spark erosion) techniques to form an attachment surface.

It is known that metals such as titanium and its alloys, from which implants are often made, are susceptible to degradation under the process conditions used to form these attachment surfaces, thereby imparting possible fatigue stress. By treating the outer sleeve used in the present invention, the main mechanical strength of the implant provided by the socket cup and stem component, remains unaffected.

The outer sleeve may comprise a homogeneous material or a heterogeneous composite such as a metal-ceramics or metal-plastics composite. The sleeve may also be coated with hydroxyapatite or another known bone growth stimulator.

BRIEF DESCRIPTION OF THE DRAWINGS

The invention will now be described with reference to the accompanying drawings in which:

FIGS. 2a, 2b and 2c are diagrammatic representations of a shoulder joint incorporating the implant of FIG. 1 and illustrate the improved articulation of such a replacement joint. FIGS. 2a and 2b illustrates lateral abduction in the frontal plane and FIG. 2c adduction (the sleeve of the implant has been omitted for purposes of clarity).

DETAILED DESCRIPTION OF PREFERRED EMBODIMENTS

Figure 1:
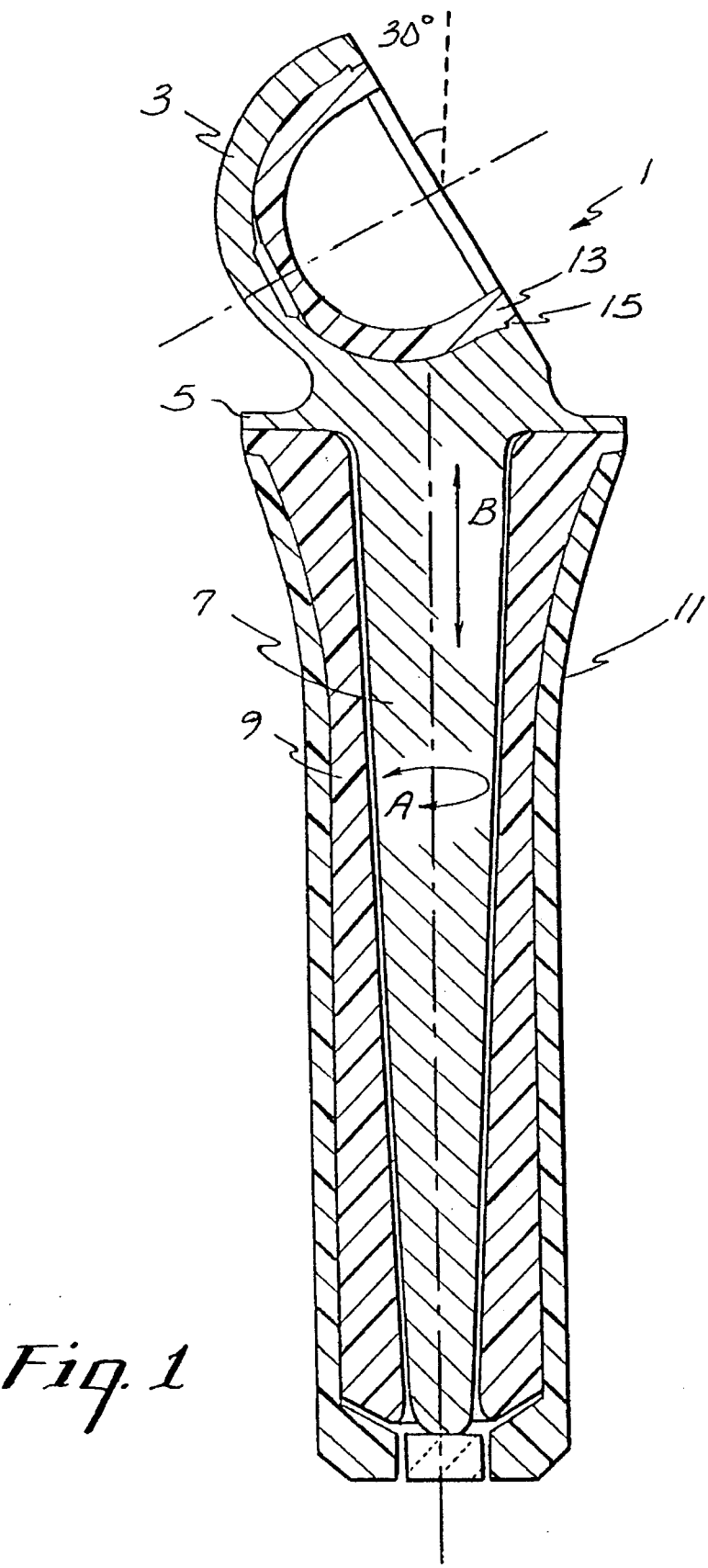
FIG. 1 is a vertical section through the humeral implant in accordance with the invention.

Referring to FIG. 1, humeral implant (1) comprises integral socket cup (3), collar (5) and elongate stem (7) located within inner sleeve (9) and outer sleeve (11). The stem (7), inner sleeve (9) and outer sleeve (11) are shaped so as to have a complimentary fit within one another, the stem (7) being rotatable and axially displaceable within inner sleeve (9). Outer sleeve (11) engages the inner sleeve (9) to prevent rotation of the same. The implant (1) is used to replace a patient's natural humeral head which is removed prior to insertion. The methods for removal of the humerus head, treatment of the humerus and installation of the implant (1) are known in the art. With the exception of inner sleeve (9), the implant (1) is preferably fabricated from titanium or a titanium alloy, the inner sleeve (9) comprising a high density plastics material such as polyethylene. Socket cup (3) is located on the proximal portion of stem (7) and has a rake of 30° to the longitudinal axis of the stem (7) and contains a plastics cup liner (13). A lip (15) on the socket cup (3) engages a complimentary rib on liner (13) to ensure a permanent fit. The inner surface of the fitted liner (13) conforms exactly to the dimensions of the glenoid component (17) (FIGS. 2a, b and c and 3).

Stem (7) is capable of rotational movement (represented by arrow A) and axial movement (represented by arrow B) within inner sleeve (9) to compensate for the humeral rotation and/or relocation required by the shoulder joint. Typically, the axial movement is in the range 1 to 3 cm. The stem (7) is of sufficient length to prevent dislocation of the joint under normal distraction of the component parts in situ. To prevent the stem (7) bedding into the inner sleeve (9) subsequent to fitting, the stem is provided with collar (5).

Figure 2A:
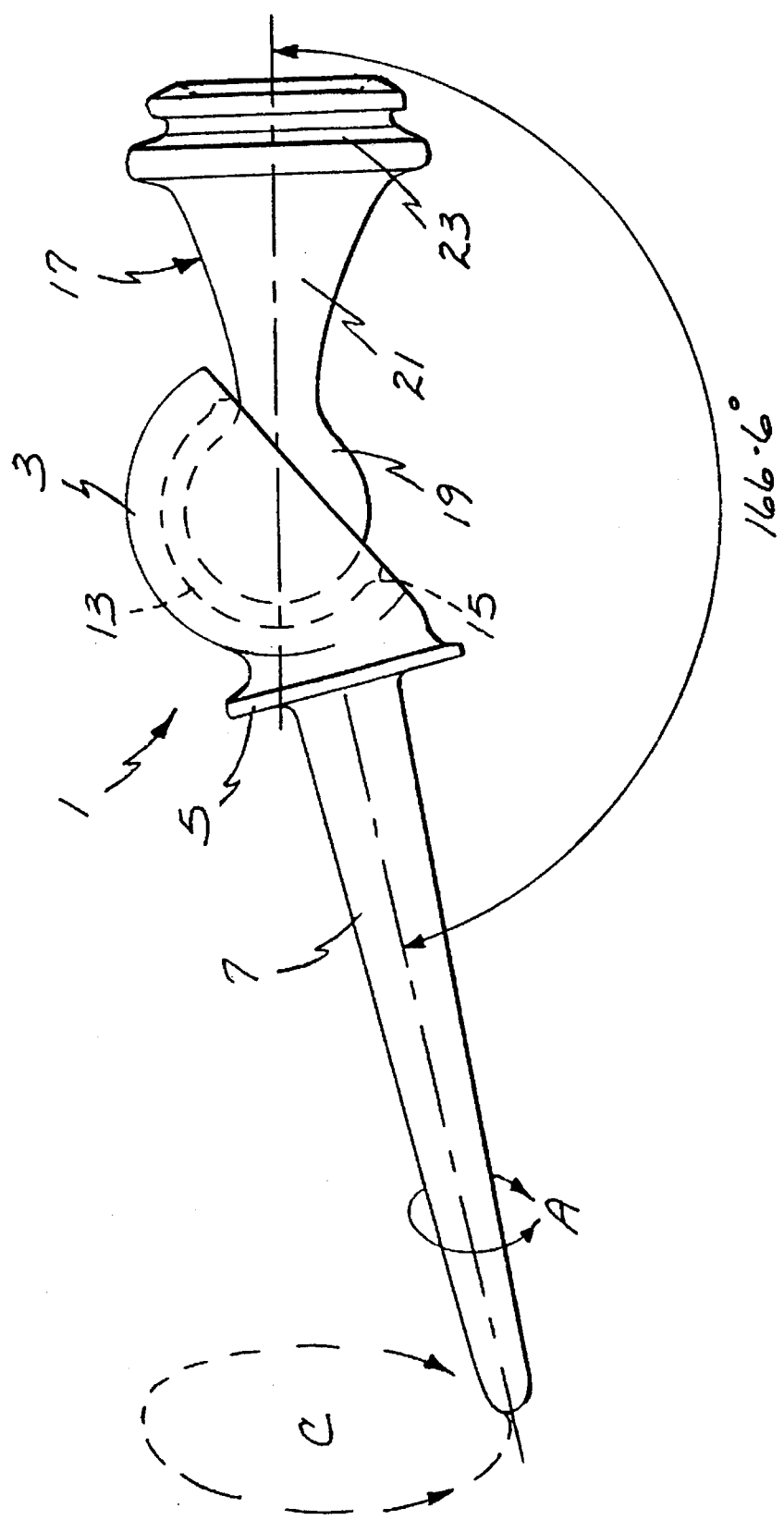
Figure 2C:
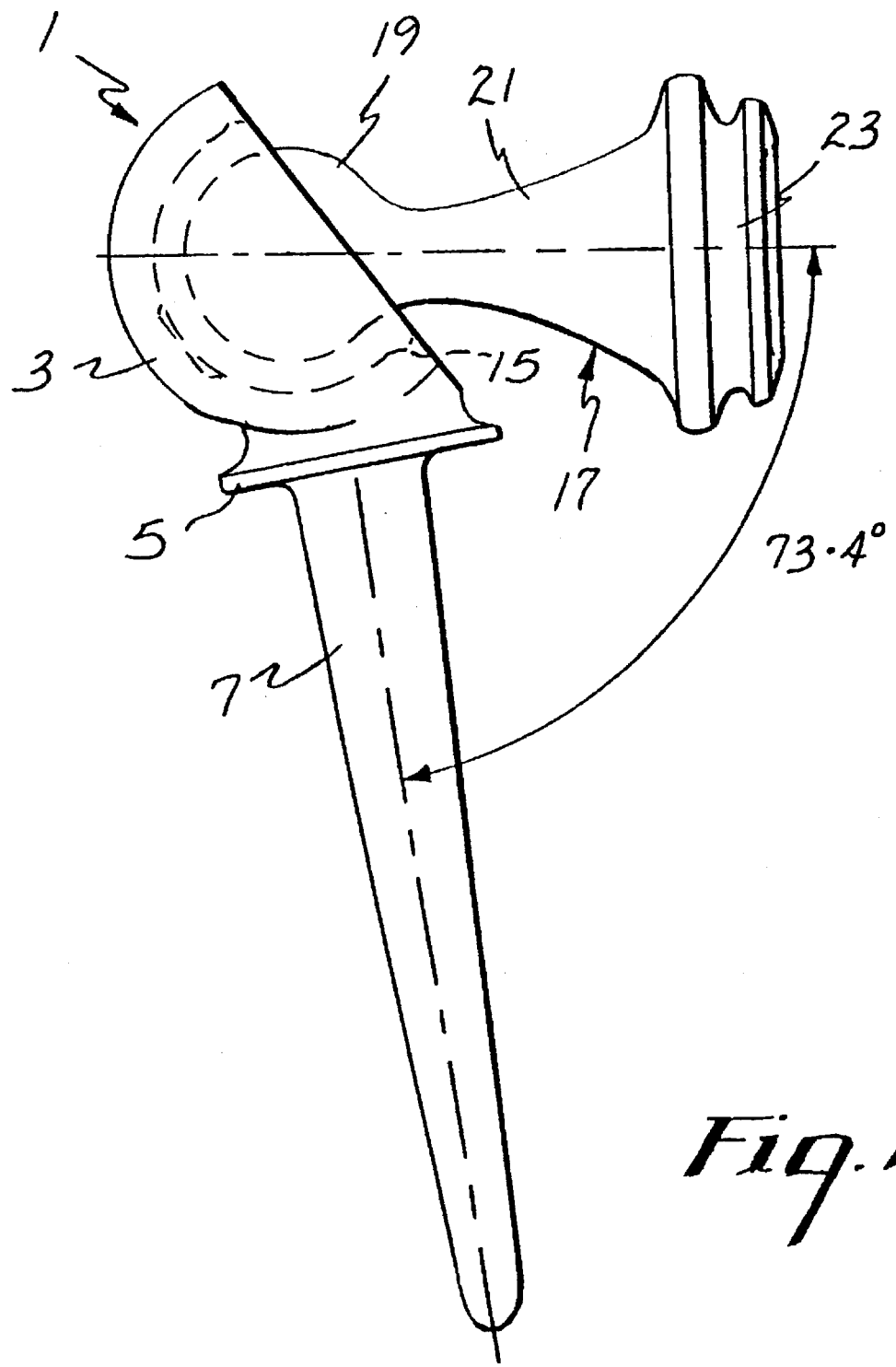

The articulation of a replacement shoulder joint incorporating a humeral implant (1) in accordance with the invention is shown by FIGS. 2a, 2b and 2c. The shoulder joint is an inverted ball and socket arrangement of glenoid prosthesis (17) comprising head (19), neck (21) and body (23), and humeral implant (1). Only the socket cup (3), collar (5) and elongate stem (7) of the implant are shown, the sleeves (9) and (11) being omitted to illustrate the rotational freedom of the shoulder joint. Socket cup (3) is inclined at an angle of 30° to the longitudinal axis of stem (7).

From FIG. 2a, the shoulder joint is capable of a full lateral abduction of at least 166° in the frontal plane. This is equivalent to effecting a movement with the outstretched right arm held approximately horizontally (i.e., shoulder height). As the arm is abducted further towards the vertical, as illustrated in FIG. 2b, rather than levering the joint components apart, as would be expected with known glenohumeral implants, the stem (7) is free to articulate, not only around the glenoid head (19), as shown by arrow C, but also within the sleeve (9) and (11) itself, as shown by arrow A. This allows for a smooth and continuous transition through all angles of abduction (and subsequent adduction). The limitation of known shoulder joints for movement caused by contact between the lip of socket cup (3) and glenoid neck (21) is thus compensated for by independent rotation of stem (7) within the sleeve.

A potential no-go region of 14° either side of the horizontal arm location is enough to be unconsciously compensated for by minor movements of the scapula. Alternatively, a steeper rake to the cup angle, to 40° rather than 30°, would also compensate for the slight anterior or posterior rotation of the arm which would be experienced as the simultaneous biaxial rotations of the humeral component took place (assuming that the scapula were completely immobile).

Referring to FIG. 2c, maximum adduction is as good as a normal shoulder joint, being approximately 16°, equivalent to touching the left shoulder blade with the right hand passing across the chest (with scapular compensation). As such, shoulder replacements incorporating implants of the invention are found not to stress the patient's normal muscular and scapular function. Equally, acromial and coracoid interference are normal.

The axial movement of the stem (7) within the sleeve (9) shown by the arrow B in FIG. 1 absorbs humeral distraction thereby preventing the joint from potential dislocating forces. For example, if a heavy weight is carried the force will not be transmitted directly to the glenoid prosthesis (17) via the humeral implant (1) which could cause dislocation, but movement of the humerus relative to the stem (7) and socket cup (3) is allowed so that the muscles of the shoulder and arm take the strain of the load.

The ability of movement of the stem (7) within the sleeve (9) has the additional advantage that the criticality of alignment of gleno-humeral shoulder replacement is reduced since the movement is readily able to compensate for minor inaccuracies in the alignment.

Figure 3:
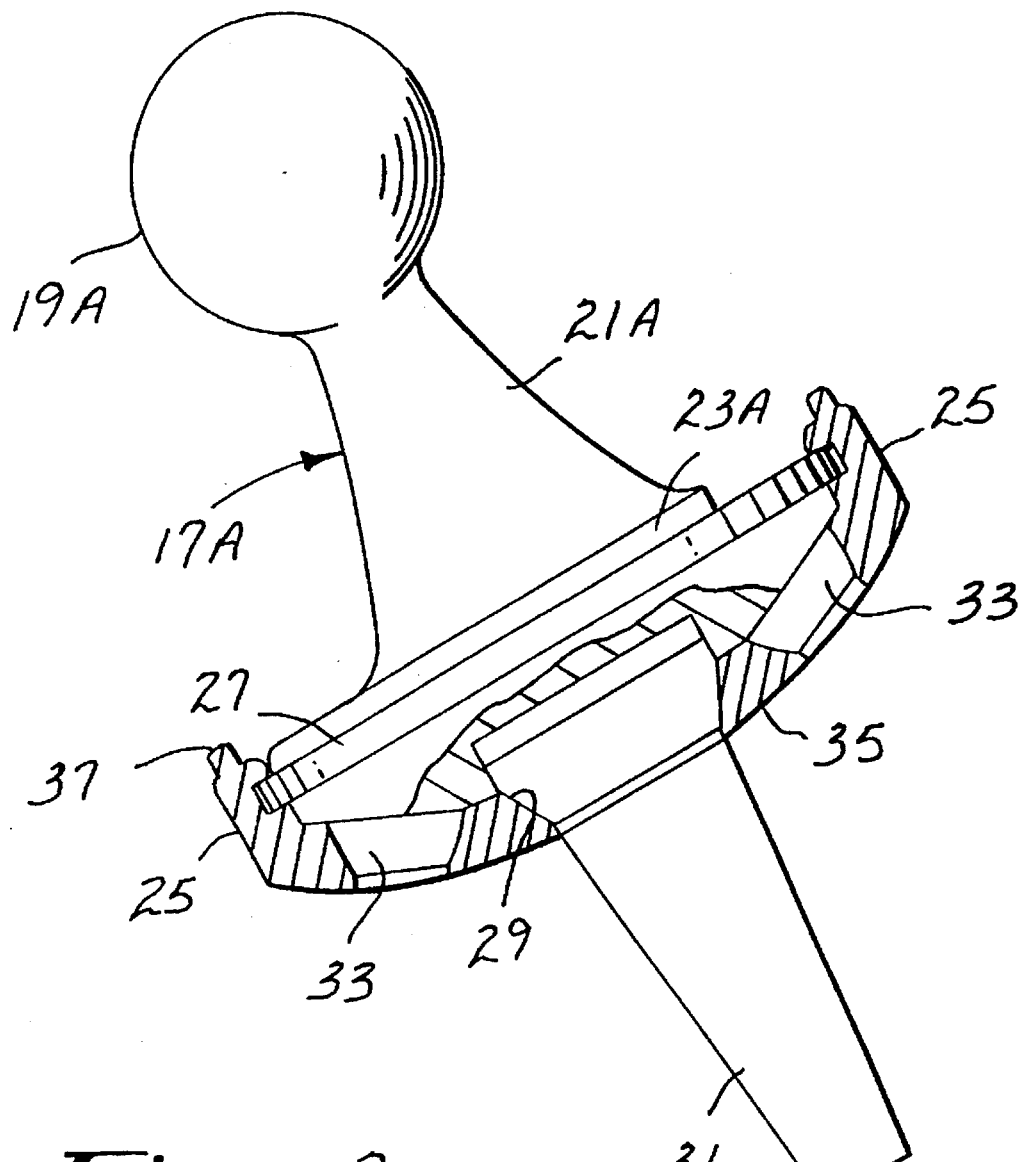
FIG. 3 shows a glenoid component of the invention.

FIG. 3 shows one embodiment of the glenoid prosthesis, here designated (17A), in which the body (23A) of the glenoid component (17A) is mounted on a backing plate (25) by a circlip (27). (Features shown in FIG. 3 that correspond to features in FIGS. 2a, 2b and 2c are designated by the same reference numeral with the addition of the letter "A".) The backing plate (25) includes a central screw-receiving opening (29) for receiving a central screw (31) shown in phantom, and a plurality (e.g., 4) screw-receiving openings (33) spaced from the central screw-receiving opening (29). An attachment surface (not shown) may be provided on the outer surface (35) of the backing plate (25) to facilitate ingrowth of bone, and an annular lip (37) may be provided to facilitate mounting a plastic liner (not shown) to adapt the backing plate (25) for use as another type of glenoid prosthesis. It is contemplated that the glenoid component (17A), circlip (27) and backing plate (25) will be formed of titanium, possibly with a hydroxyapatite coating (not shown) along the outer surface (35) of the backing plate (25).

As various changes could be made in the above constructions and methods without departing from the scope of the invention, it is intended that all matter contained in the above description or shown in the accompanying drawing be interpreted as illustrative and not in a limiting sense.

We claim:

1. A humeral implant of the type that locates the head of a glenoid prosthesis relative to a patient's humerus, the implant comprising:

a socket cup having an opening adapted to receive the head of the glenoid prosthesis, the opening of the socket cup defining a diametrical plane;

an elongate stem connected to the socket cup, with the diametrical plane of the socket cup disposed at an angle to the longitudinal axis of the stem; and an elongate sleeve adapted to receive the elongate stem and allow rotary and axial movement of the elongate stem within the sleeve such that the opening and the diametrical plane of the socket cup face in different directions as the stem rotates, thereby permitting substantially greater rotation of the elongate stem relative to the head of the glenoid prosthesis than would be the case if the elongate stem were not permitted to rotate within the sleeve, the sleeve being adapted to be inserted and secured within the humerus of the patient.

2. An implant as claimed in claim 1 in which the diametrical plane of the socket cup is disposed at an angle of from 20° to 40° to the longitudinal axis of the stem.

3. An implant as claimed in claim 2 further comprising a collar portion interposed between the socket cup and the elongate stem, the collar portion having a dimension greater than that of the bore of the sleeve.

4. An implant as claimed in claim 3 fabricated from titanium or a titanium alloy.

5. An implant as claimed in claim 1 comprising an inner sleeve interposed between the elongate stem and an outer sleeve, the elongate stem being capable of movement within the inner sleeve.

6. An implant as claimed in claim 5 in which the inner sleeve is formed of a high density plastics material.

7. A shoulder joint prosthesis according to claim 8 in which the diametrical plane of the socket cup is disposed at an angle from 20° to 40° to the longitudinal axis of the stem.

8. A shoulder joint prosthesis comprising a glenoid component having a head adapted to be secured to the patient and a humeral implant comprising:

a socket cup having an opening adapted to receive the head of the glenoid prosthesis, the opening of the socket cup defining a diametrical plane;

an elongate stem connected to the socket cup, with the diametrical plane of the socket cup disposed at an angle to the longitudinal axis of the stem; and an elongate sleeve adapted to receive the elongate stem and allow rotary and axial movement of the elongate stem within the sleeve such that the opening and the diametrical plane of the socket cup face in different directions as the stem rotates, thereby permitting substantially greater rotation of the elongate stem relative to the head of the glenoid prosthesis than would be the case if the elongate stem were not permitted to rotate within the sleeve, the sleeve being adapted to be inserted and secured within the humerus of the patient.

9. A shoulder joint prosthesis according to claim 7 further comprising a collar portion interposed between the socket cup and the elongate stem, the collar portion having a dimension greater than that of the bore of the sleeve.

10. A shoulder joint prosthesis according to claim 9 fabricated from titanium or a titanium alloy.

11. A shoulder joint prosthesis according to claim 8 comprising an inner sleeve interposed between the elongate stem and an outer sleeve, the elongate stem being capable of movement within the inner sleeve.

12. A shoulder joint prosthesis according to claim 11 in which the inner sleeve is formed of a high density plastics material.

13. An implant as claimed in claim 2 in which the outer surface of the sleeve comprises an attachment surface for ingrowth of bone tissue.

14. A shoulder joint prosthesis according to claim 9 in which the outer surface of the sleeve comprises an attachment surface for ingrowth of bone tissue.

15. A method of raising and lowering a humeral component of a shoulder joint prosthesis relative to the glenoid component of the shoulder joint prosthesis to facilitate movement of a patient's arm through a wide range of motion, the method comprising the following steps:

providing the patient with a shoulder joint prosthesis including a glenoid component having a head and a humeral component comprising a socket cup having an opening adapted to receive the head of the glenoid prosthesis, the opening of the socket cup defining a diametrical plane, an elongate stem connected to the socket cup such that the diametrical plane of the socket cup is disposed at an angle to the diametrical plane of the stem, and an outer sleeve adapted to rotatably receive the elongate stem for rotation of the stem around its longitudinal axis, the glenoid component being secured to the glenoid process of the patient and the outer sleeve being secured within the humerus of the patient, the elongate stem being allowed to move axially within the sleeve;

raising the humeral component through an arc centered on the head of the glenoid component while allowing the socket cup to articulate relative to the longitudinal axis of the stem, thereby causing the opening and diametrical plane of the socket cup to face in different directions to permit greater movement of the humeral component relative to the glenoid component to facilitate movement of the patient's arm through a wide range of motion; and loading the patient's arm in tension while allowing the elongate stem to move axially within the sleeve in response to the load to prevent transmission of the load through the prosthesis.

16. A method as claimed in claim 15 in which the socket cup is disposed at an angle of from 20° to 40° to the longitudinal axis of the stem, and the step of raising the humeral component includes allowing the socket cup to articulate between positions in which the socket cup faces generally upwardly and positions in which the socket cup faces generally downwardly as the humeral component is raised and lowered.

* * * * *